(12) United States Patent
Kilbey

(10) Patent No.: US 7,618,390 B2
(45) Date of Patent: Nov. 17, 2009

(54) EQUINE BANDAGE WITH VENTRAL ACCESS OPENING

(76) Inventor: Bryan E. Kilbey, 54 Hugh Adams Rd., DeFuniak Springs, FL (US) 32435

( * ) Notice: Subject to any disclaimer, the term of this patent is extended or adjusted under 35 U.S.C. 154(b) by 234 days.

(21) Appl. No.: 11/725,616

(22) Filed: Mar. 20, 2007

(65) Prior Publication Data
US 2008/0015483 A1  Jan. 17, 2008

Related U.S. Application Data

(60) Provisional application No. 60/784,335, filed on Mar. 21, 2006.

(51) Int. Cl.
*A61L 15/00* (2006.01)
*A61F 13/00* (2006.01)
*A61F 13/06* (2006.01)
*A61D 3/00* (2006.01)
*A01K 13/00* (2006.01)
*B68C 5/00* (2006.01)
*A61B 19/00* (2006.01)
*A61F 5/37* (2006.01)

(52) U.S. Cl. ............ 602/75; 602/44; 602/65; 602/76; 602/78; 119/850; 119/857; 119/863; 119/865; 119/816; 119/725; 119/728; 128/853; 128/854; 128/869; 128/870; 128/872; 128/875; 128/876; 54/79.1; 54/79.2; 54/79.4

(58) Field of Classification Search ............ 54/79.1, 54/79.2, 79.4; 119/725, 728, 850, 857, 863; 119/865, 816; 602/44, 65, 76, 78, 75; 128/853, 128/854, 869, 870, 872, 875–876
See application file for complete search history.

(56) References Cited

U.S. PATENT DOCUMENTS

| | | | | | |
|---|---|---|---|---|---|
| 5,271,211 A | * | 12/1993 | Newman | ............ | 54/79.2 |
| 6,009,693 A | * | 1/2000 | Hsi-Chang | ............ | 54/79.1 |
| 2004/0237480 A1 | * | 12/2004 | Keiner | ............ | 54/79.2 |

* cited by examiner

*Primary Examiner*—Patricia M Bianco
*Assistant Examiner*—Tarla R Patel
(74) *Attorney, Agent, or Firm*—J. Wiley Horton

(57) ABSTRACT

An integrated bandaging system for encircling the abdomen of a horse. A ventral access opening selectively provides access to the horse's abdomen while the bandage remains in place. This ventral access opening is normally covered by a ventral window cover. However, the window cover may be easily opened so that an old dressing can be removed, an abdominal wound can be cleaned, and a new dressing applied. The invention has four major components: a main wrap, a saddle bridge, a ventral window cover, and a brace. The main wrap is easily placed around the horse's abdomen and secured using VELCRO® fasteners. It includes the ventral access opening. The saddle bridge attaches over the top of the main wrap and adjustably applies tension to the horse's mid section. The ventral window cover attaches over the ventral access opening and provides further adjustment of the tension on the abdomen. The brace applies over the points of the horse's shoulders, between the front legs, and over the ventral chest region. This final component prevents the bandage from slipping aft on the horse.

14 Claims, 21 Drawing Sheets

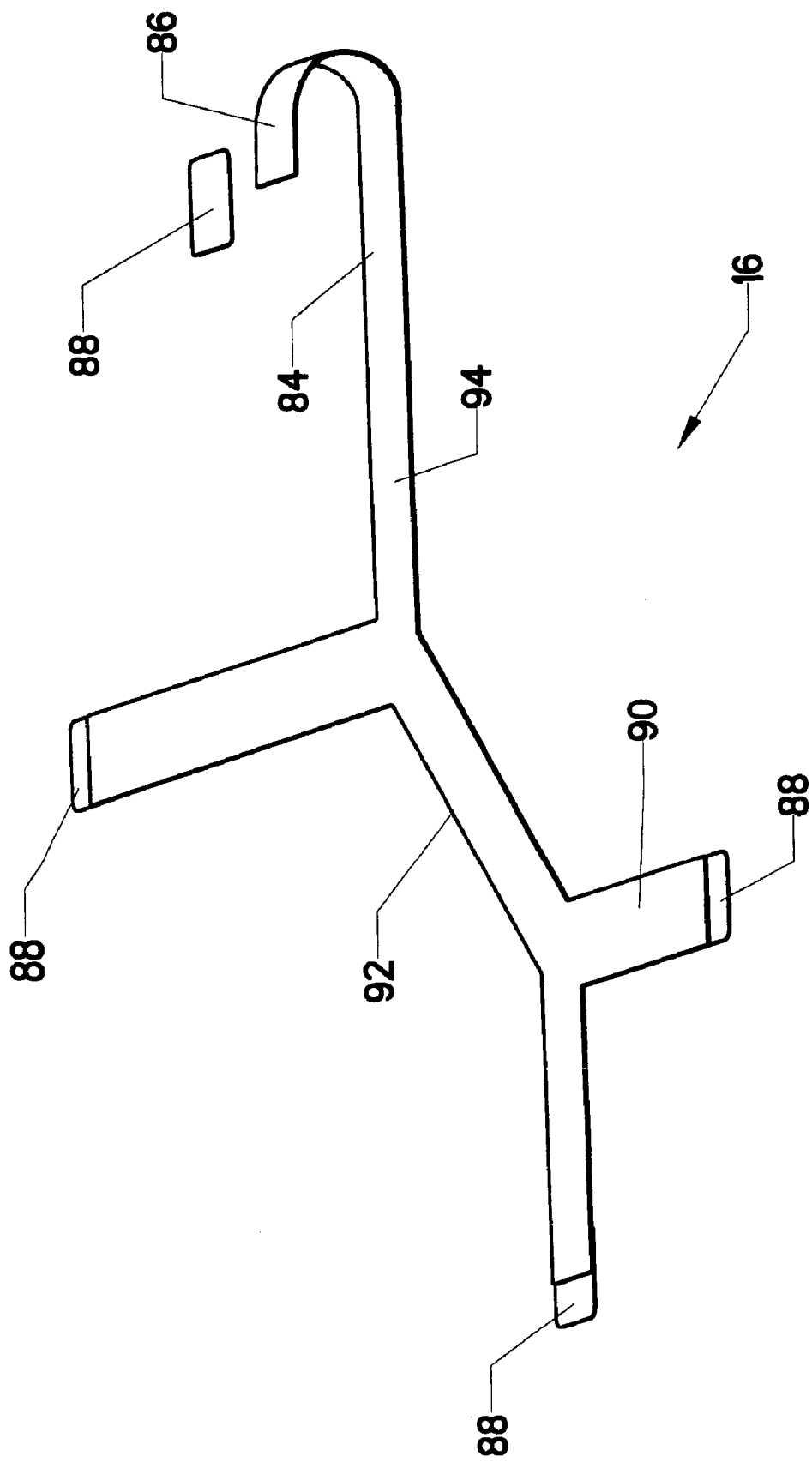

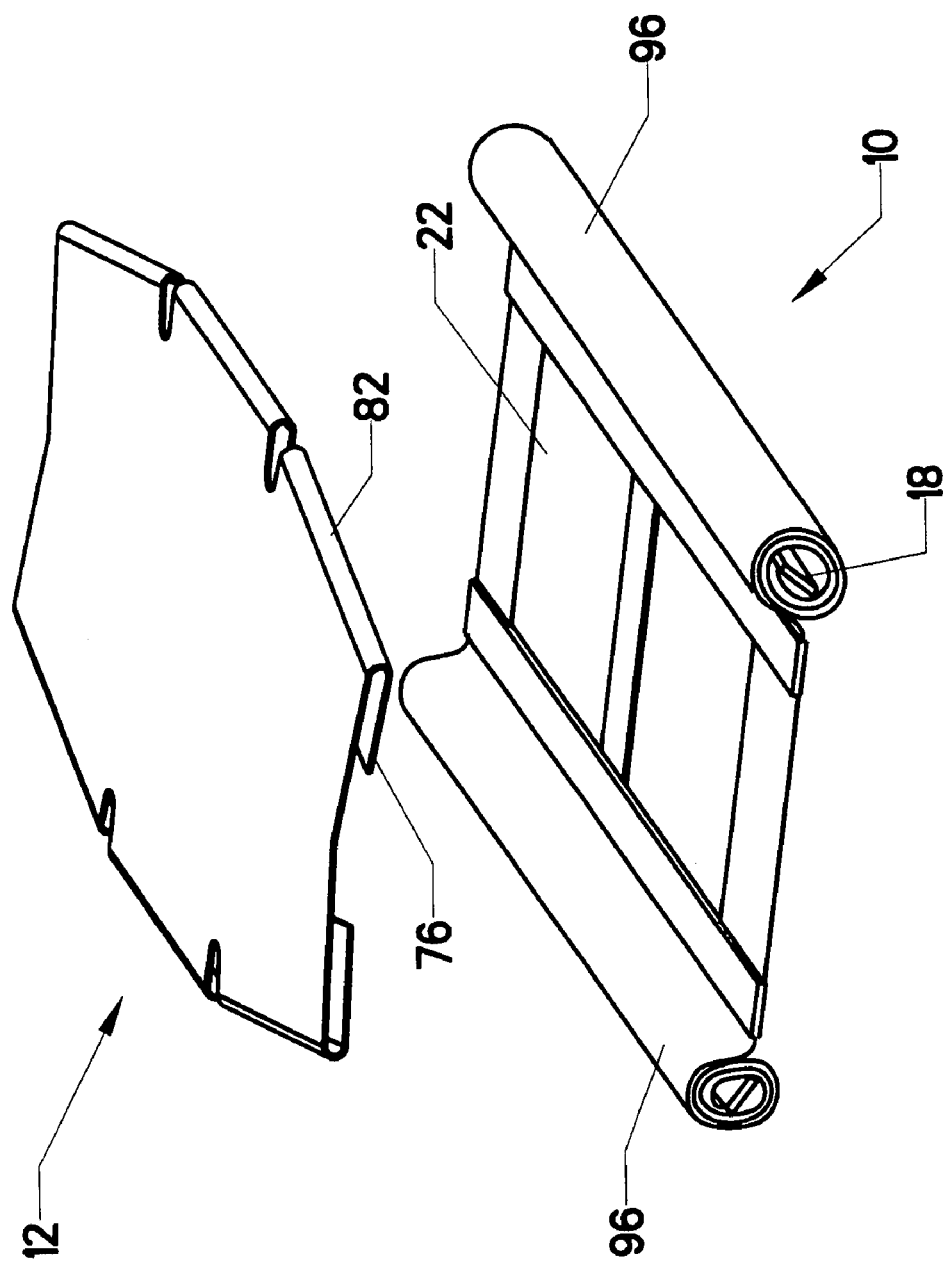

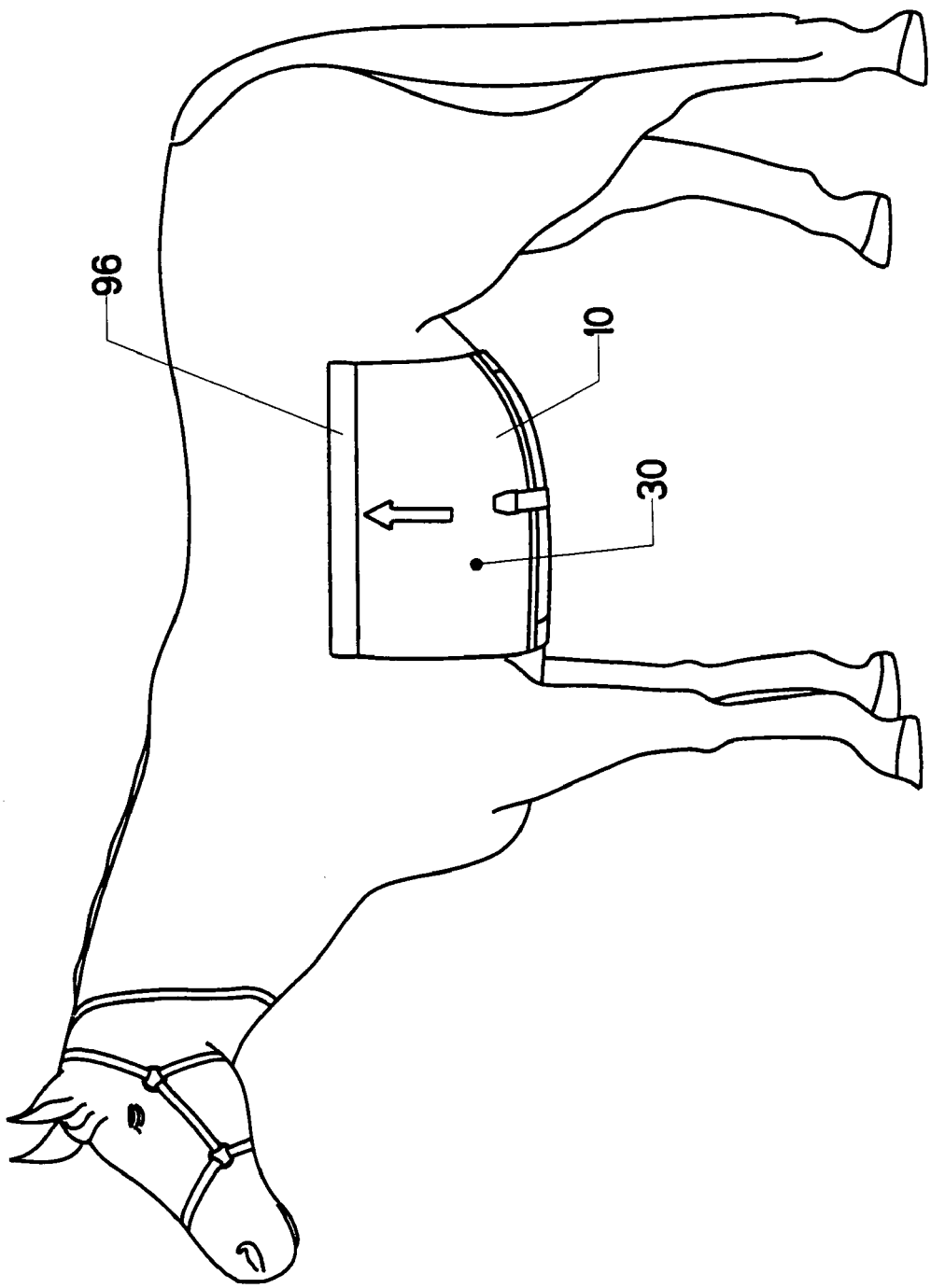

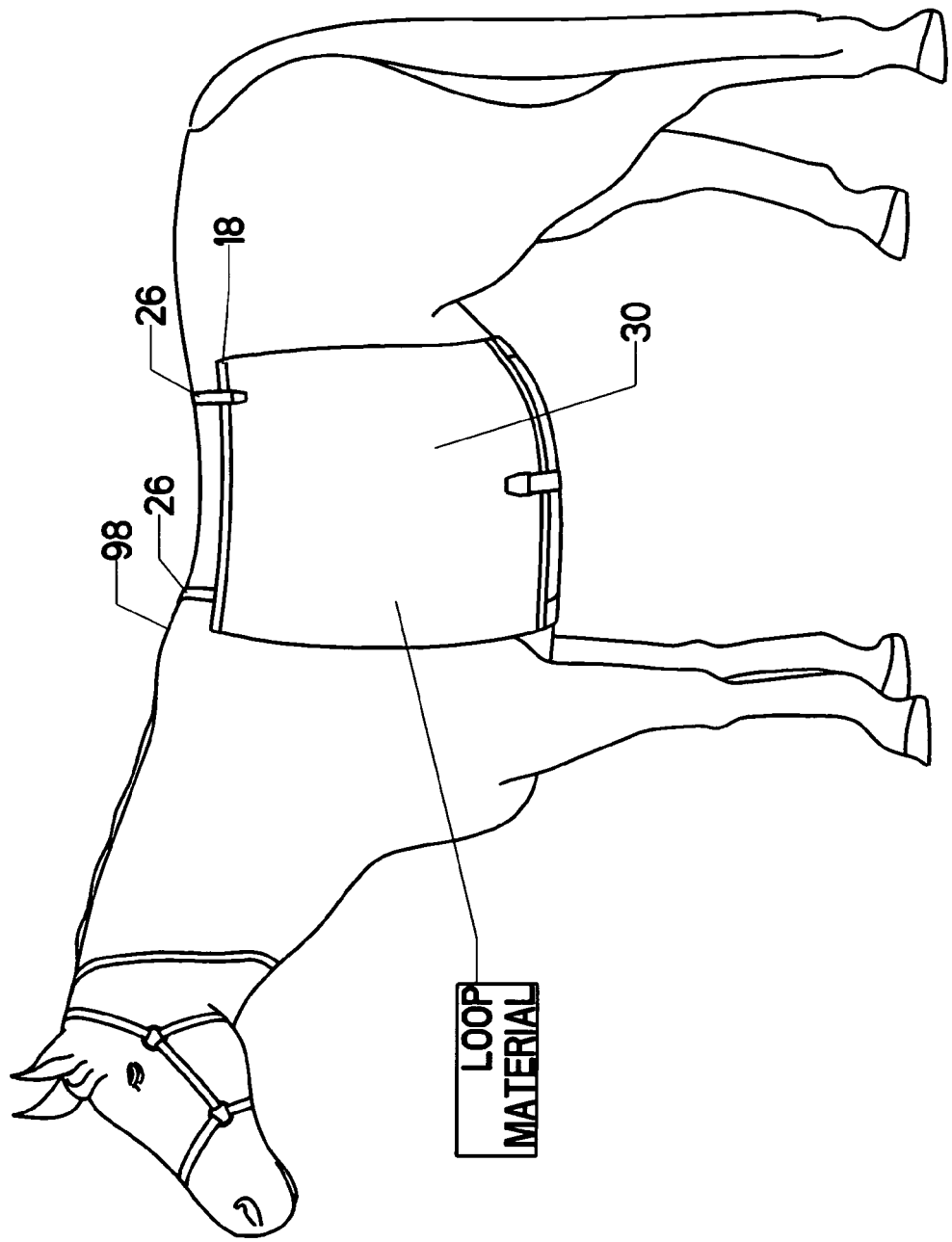

EQUINE BANDAGE WITH VENTRAL ACCESS OPENING

This is a non-provisional patent application claiming the benefit of an earlier-filed provisional application. The earlier-filed application was filed on Mar. 21, 2006. It listed the same inventor. It was assigned Application Ser. No. 60/784,335.

CROSS-REFERENCES TO RELATED APPLICATIONS

None.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of veterinary medicine. More specifically, the invention comprises an equine bandage with a ventral access opening which allows access to the ventral portion of a horse while the bandage remains in position.

2. Description of the Related Art

Ventral wounds in horses have traditionally been difficult to secure. A good example is an abdominal surgical incision. The incision must be covered to prevent the horse disturbing the site. However, dressings over the incision must be frequently changed in order to remove contaminated effluent and prevent infection. One traditional approach has been to place a compressive dressing over the incision, then wrap the horse's abdomen in elastic bandages.

If properly applied, the elastic bandages can remain in place on the horse. They also provide compression to the abdomen, which tends to keep the incision closed. However, since the wound dressing must typically be changed daily, the entire wrapping process must be frequently repeated. This "rebandaging" process is complex and time consuming. One person must hold the dressing in place while two or more additional persons hold the horse and pass a lengthy elastic bandage many times around the horse's abdomen.

In addition, while the bandage is off the horse during this process, there is a risk of abdominal rupture. A horse's physiology places the abdominal wall in considerable tension. Staples or sutures placed to close an abdominal incision are often highly stressed as a result. The incision closure may therefore fail without the compressive assistance of the bandage wrap. Thus, every time the dressing must be changed, there is a risk that the incision closure will fail.

BRIEF SUMMARY OF THE PRESENT INVENTION

The present invention comprises an integrated bandaging system for encircling the abdomen of a horse. A ventral access opening selectively provides access to the horse's abdomen while the bandage remains in place. This ventral access opening is normally covered by a ventral window cover. However, the window cover may be easily opened so that an old dressing can be removed, an abdominal wound can be cleaned, and a new dressing applied.

The invention has four major components: a main wrap, a saddle bridge, a ventral window cover, and a brace. The main wrap is easily placed around the horse's abdomen and secured using VELCRO® fasteners. It includes the ventral access opening. The saddle bridge attaches over the top of the main wrap and adjustably applies tension to the horse's mid section. The ventral window cover attaches over the ventral access opening and provides further adjustment of the tension on the abdomen. The brace applies over the points of the horse's shoulders, between the front legs, and over the ventral chest region. This final component prevents the bandage from slipping aft on the horse.

When access to the horse's abdomen is desired, the ventral window cover may be opened. Access is provided while the balance of the bandaging system remains in place. Thus, the horse's abdomen is externally reinforced at all times.

BRIEF DESCRIPTION OF THE SEVERAL VIEWS OF THE DRAWINGS

FIG. 8 is a perspective view, showing the components of the brace.

FIG. 9 is a perspective view, showing how the main wrap and saddle bridge can be configured just prior to installation on a horse.

FIG. 10 is a perspective view, showing installation of the main wrap on a horse.

FIG. 11 is a perspective view, showing the securing of the main wrap to a horse.

Reference Numerals In The Drawings

| 10 | main wrap | 12 | saddle bridge |
|---|---|---|---|
| 14 | ventral window cover | 16 | brace |
| 18 | rolling stay | 20 | window stay |
| 21 | first lateral ventral edge | 22 | ventral window |
| 23 | second lateral ventral edge | 24 | mesh panel |
| 25 | first lateral dorsal edge | 26 | bridging strap |
| 27 | second lateral dorsal edge | 28 | inner surface |
| 30 | outer surface | 32 | inner surface |
| 34 | outer surface | 36 | inner surface |
| 38 | outer surface | 40 | front strap |
| 42 | hook tab | 44 | middle strap |
| 46 | rear strap | 48 | hook tab |
| 50 | opening | 52 | dart seam |
| 54 | hook panel | 56 | lanyard |
| 58 | front tab | 60 | middle tab |
| 62 | rear tab | 64 | central portion |
| 66 | central portion | 68 | dart seam |
| 70 | hook panel | 72 | lanyard |
| 74 | loop panel | 76 | front tab |
| 78 | middle tab | 80 | rear tab |
| 82 | fold | 84 | inner surface |
| 86 | outer surface | 88 | hook panel |
| 90 | lower wing | 92 | sternal bridge |
| 94 | upper wing | 96 | roll |
| 97 | stay pocket | 98 | withers |
| 100 | point of shoulder | 102 | carotid notch |
| 104 | dressing | | |

DESCRIPTION OF THE INVENTION

Figure 1:
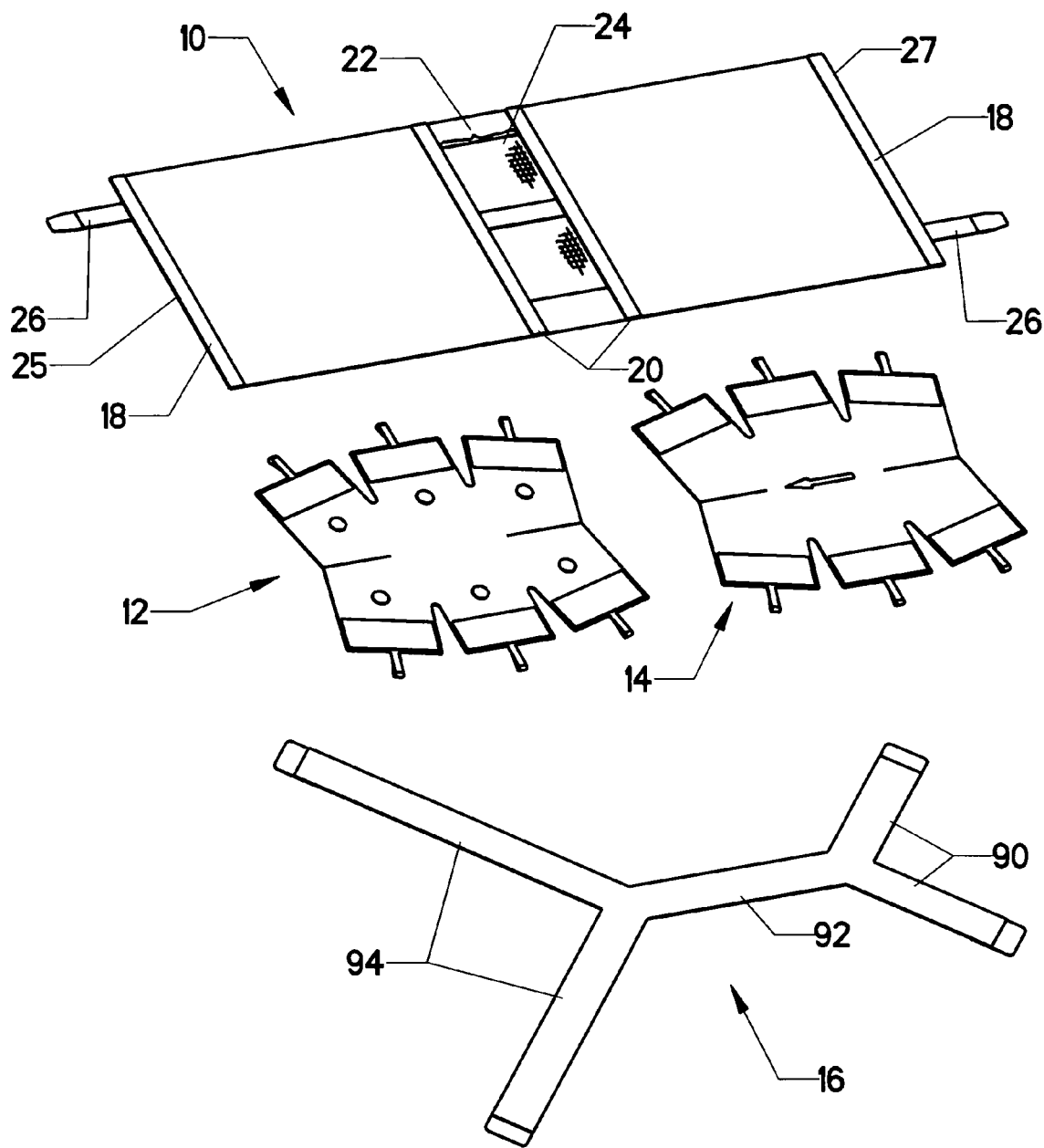
FIG. 1 is a perspective view showing the major components of the present invention.

The invention includes several large components which are assembled on the horse. These components are shown laid out flat in FIG.1. Main wrap 10 is sized to pass around a horse's mid section. It is made of a flexible and elastic fabric material. It will stretch when placed under tension. Each end features a rolling stay 18, which is a semi-rigid bar (made of material which is substantially more rigid that the elastic material of the main wrap) slipped into a stitched pocket. These rolling stays allow a user to easily grasp an end of the main wrap at a single point. The device could function without the rolling stays, but would be more cumbersome to handle. Their operation will be more fully described subsequently.

Each end of the main wrap also features a bridging strap 26 extending outward. These will be used to temporarily secure the main wrap to the horse while the other components are positioned. Ventral window 22 is located in the middle of the main wrap. The window is flanked by a pair of window stays 20. These are similar to the rolling stays, except that they maybe affixed permanently. Mesh panel 24 covers the open portion of the ventral window.

The main wrap is configured to be wrapped around the middle portion of a horse. Turning briefly to FIG.11, the reader will observe the main wrap installed on a horse. The wrap includes a large elastic panel having a dorsal region and a ventral region. The dorsal region is of course configured to fit over the dorsal region of the horse while the ventral region of the elastic panel is configured to fit over the ventral region of the horse. The dorsal region of the elastic panel is broken by a gap (which is spanned by the two bridging straps 26 in the view). The ventral region of the elastic panel includes the ventral window (which can simply be an opening in the elastic panel or a second gap in the elastic panel bridged by two or more straps).

Returning now to FIG.1, the next major component is saddle bridge 12, which attaches over the dorsal region of the horse in the position customarily occupied by a saddle. Ventral window cover 14 attaches over the horse's ventral region and covers ventral window 22. Saddle bridge 12 and ventral window cover 14 are preferably made of the same material as main wrap 10. They are both flexible and elastic.

The final major component is brace 16. It is a series of straps joined together in the configuration shown. A pair of lower wings 90 is connected to a pair of upper wings 94 by sternal bridge 92. The brace is also made of elastic and flexible material.

Figure 17:
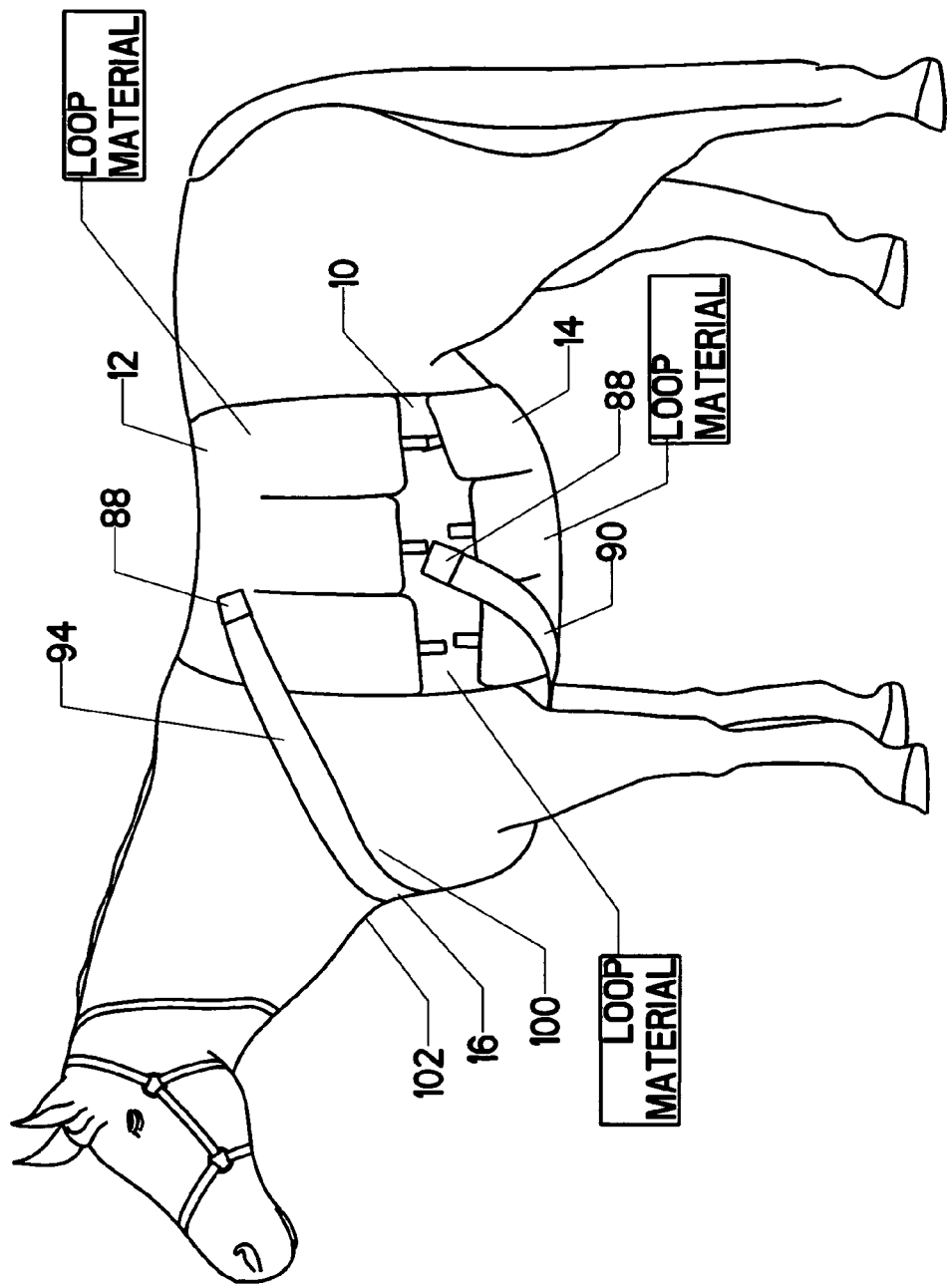
FIG. 17 is a perspective view, showing the placement of the brace.

FIG.17 shows all the components installed on a horse. By briefly studying this view, the reader may gain a helpful general understanding of where each component will ultimately be placed. Main wrap 10 passes around the horse's mid section. Saddle bridge 12 spans the top and bridges the gap in the dorsal region of the elastic panel of the main wrap (It is shown in a stretched state). Ventral window cover 14 passes around the horse's ventral region. Brace 16 passes around the two front legs.

Figure 2:
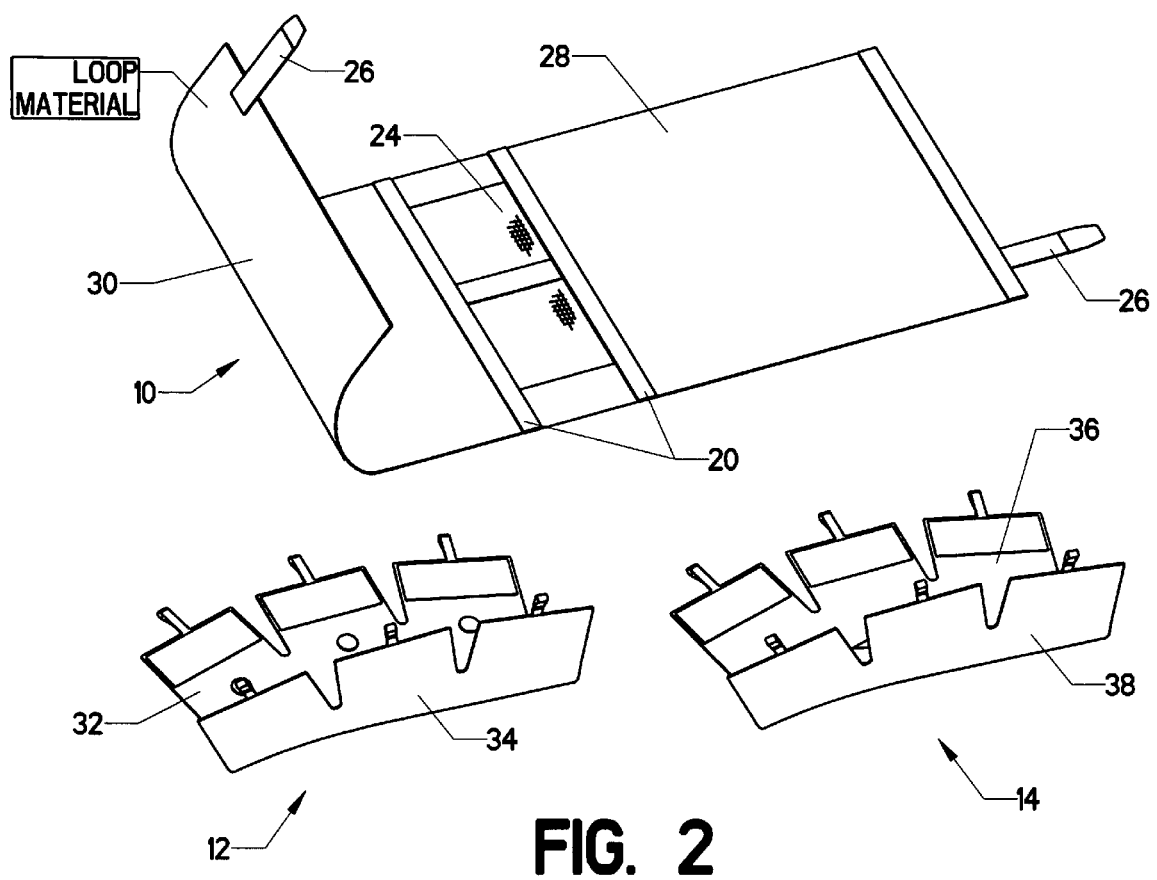
FIG. 2 is a perspective view, showing the components of FIG. 1 folded over.

FIG.2 shows the main wrap, saddle bridge, and ventral window cover in a folded state so that the reader may understand the nature of the material employed to make them. Main wrap 10 features inner surface 28 and outer surface 30. Inner surface 28 is smoothly textured. It will bear against the horse's hide, so it is preferably comfortable to a horse. Outer surface 30 is covered in fine VELCRO® loop material. ("VELCRO"® is a trademark of Velcro Industries, B.V. of the Netherlands. The trademark refers to mating pieces of fabric having hooks on one piece and loops on the other piece. When the two pieces are pressed together, the hooks mechanically interlock with the loops, thereby forming a relatively weak attachment between the two pieces). Those skilled in the art will know that some modern VELCRO® loop fabrics are quite fine. The outer surface is preferably such a fine loop. Ideally the loop structure will be tight enough to prevent the unwanted capture of lint, hairs, and dirt. Both the inner and outer surfaces must be able to stretch significantly.

Since the characteristics of the inner and outer surfaces of the main wrap must be different, it is preferable to construct the main wrap as a laminate of two different materials—one for the inner surface and one for the outer surface. Saddle bridge 12 and ventral window cover 14 are made the same way. The saddle bridge has inner surface 32 and outer surface 34, while the ventral window cover has inner surface 36 and outer surface 38.

The outer surfaces of all three components are covered in VELCRO® loop material. This loop material is designed to engage with various VELCRO® hook patches in the present invention. As an example, the two bridging straps 26 on the main wrap contain VELCRO® hook patches. If the two free ends of the main wrap are pulled toward one another (forming the main wrap into a loop), each bridging strap can be pressed against outer surface 30 on the opposite side of the gap to hold the main wrap in a loop. This will in fact be the procedure by which the main wrap is placed on the horse (described in more detail subsequently).

The inner surfaces will not engage the VELCRO® hook patches. Thus, it is important to place the inner surfaces toward the horse and the outer surfaces away from the horse. Color coding may be helpful to one installing the device. As an example, the inner surfaces can be white, while the outer surfaces can be blue.

Figure 2B:
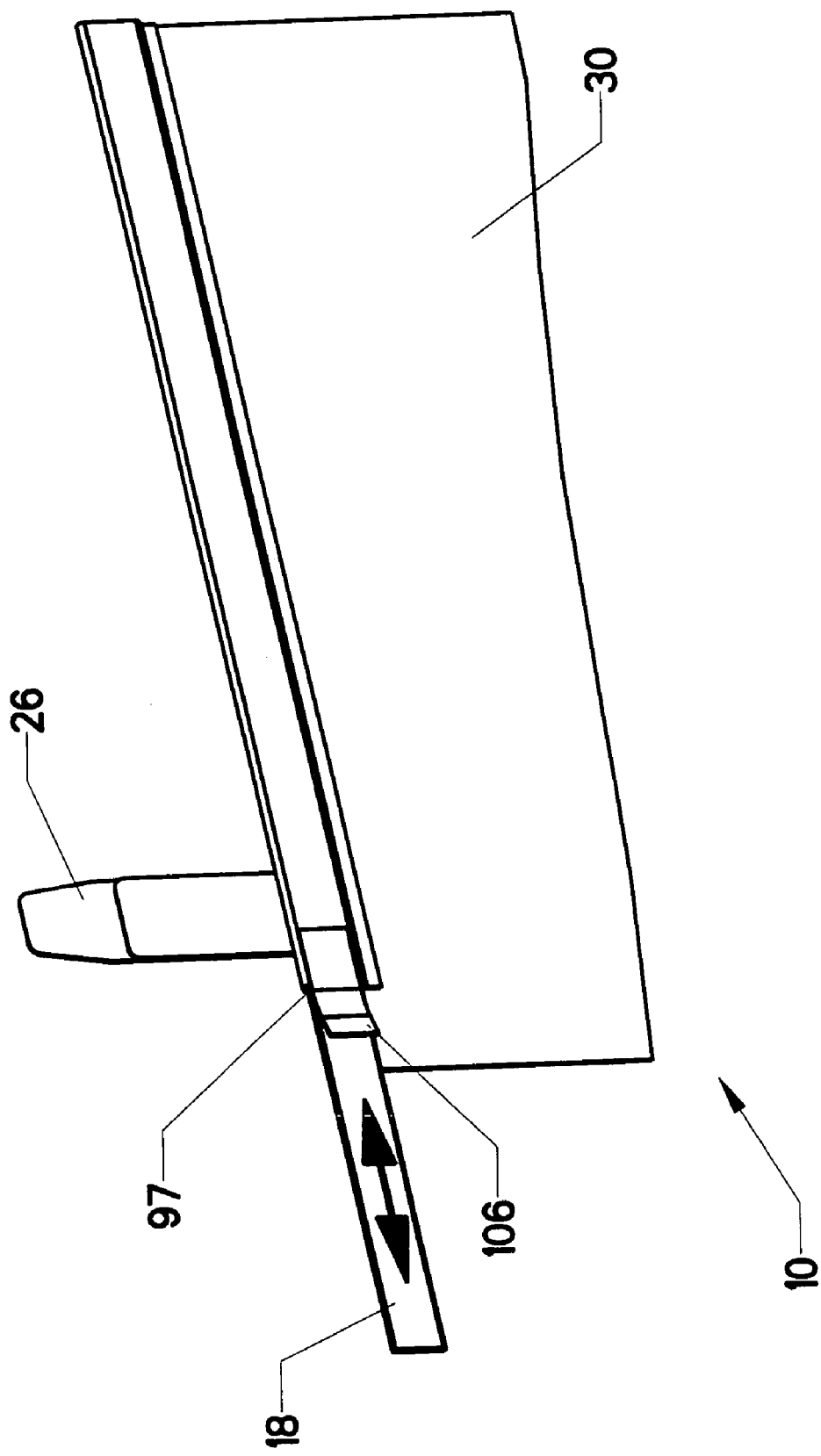
FIG. 2B is a detailed perspective view, showing how the rolling stays can be removed from the main wrap.

FIG. 2B shows the installation of the aforementioned rolling stays 18 in the main wrap. A stay pocket 97 is formed on each end of the main wrap. It is possible to slide a rolling stay 18 in and out of each stay pocket. The rolling stays are preferably semi-rigid. They can be made of a hard plastic, such as extruded ABS, or even thin aluminum bars.

Figure 3:
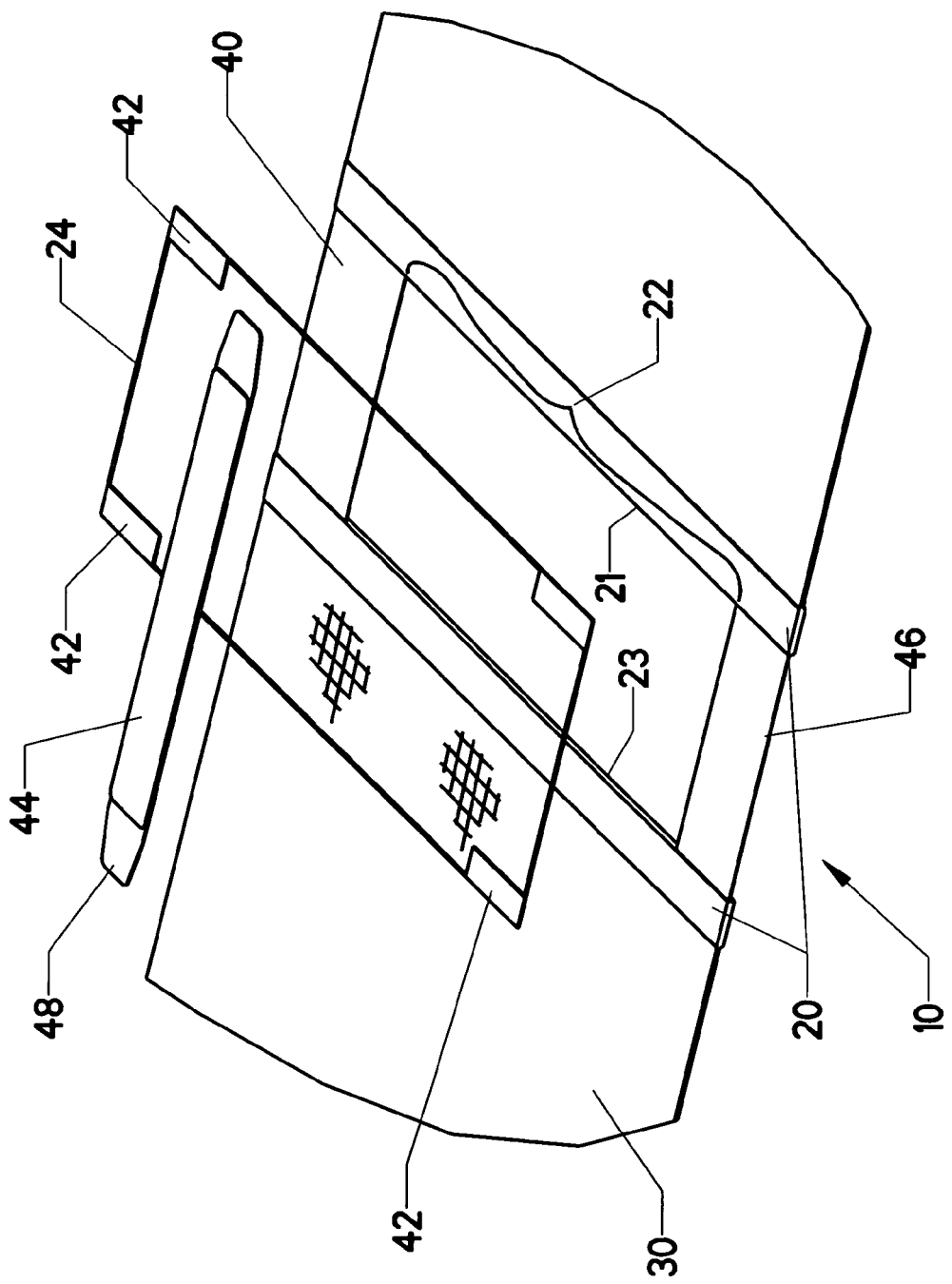
FIG. 3 is a perspective view, showing details of the ventral window in the main wrap.

An important feature of the main wrap is its ventral access window. FIG. 3 shows this component in more detail. The main wrap is preferably made of two separate elastic panels which are broken by a second gap in the ventral region. This second gap is bridged by front strap 40 and rear strap 46. As for the balance of the main wrap, the front and rear straps are made of elastic material. The two window stays 20 remain in place to prevent the middle portion of the window opening from bowing outward when tension is placed on the main wrap (such as when it is stretched around a horse's abdomen). They are attached along the two lateral ventral edges (first lateral ventral edge 21 and second lateral ventral edge 23) that define the gap in the main wrap. The reader will therefore note that the boundary of ventral window 22 is defined by a first lateral ventral edge (proximate the first window stay), front strap 40, a second lateral ventral edge (proximate the second window stay), and rear strap 46.

Mesh panel 24 covers the opening. It has a hook tab 42 at each of its four corners. When it is placed over the opening, the VELCRO® hooks on the four hook tabs stick to the VELCRO® loops covering outer surface 30. The mesh panel is preferably made of a fine mesh material—as fine as or finer than window screen. A relatively coarse depiction for the mesh is shown in the view. This is intended to be merely representational of the mesh material.

Once the mesh panel is affixed, middle strap 44 is placed over the mesh panel to reinforce the opening. It has a hook tab 48 on each end. These also engage the VELCRO® loops on outer surface 30. The middle strap is preferably made of elastic material as well, so that it can be stretched snugly across the opening.

Figure 4:
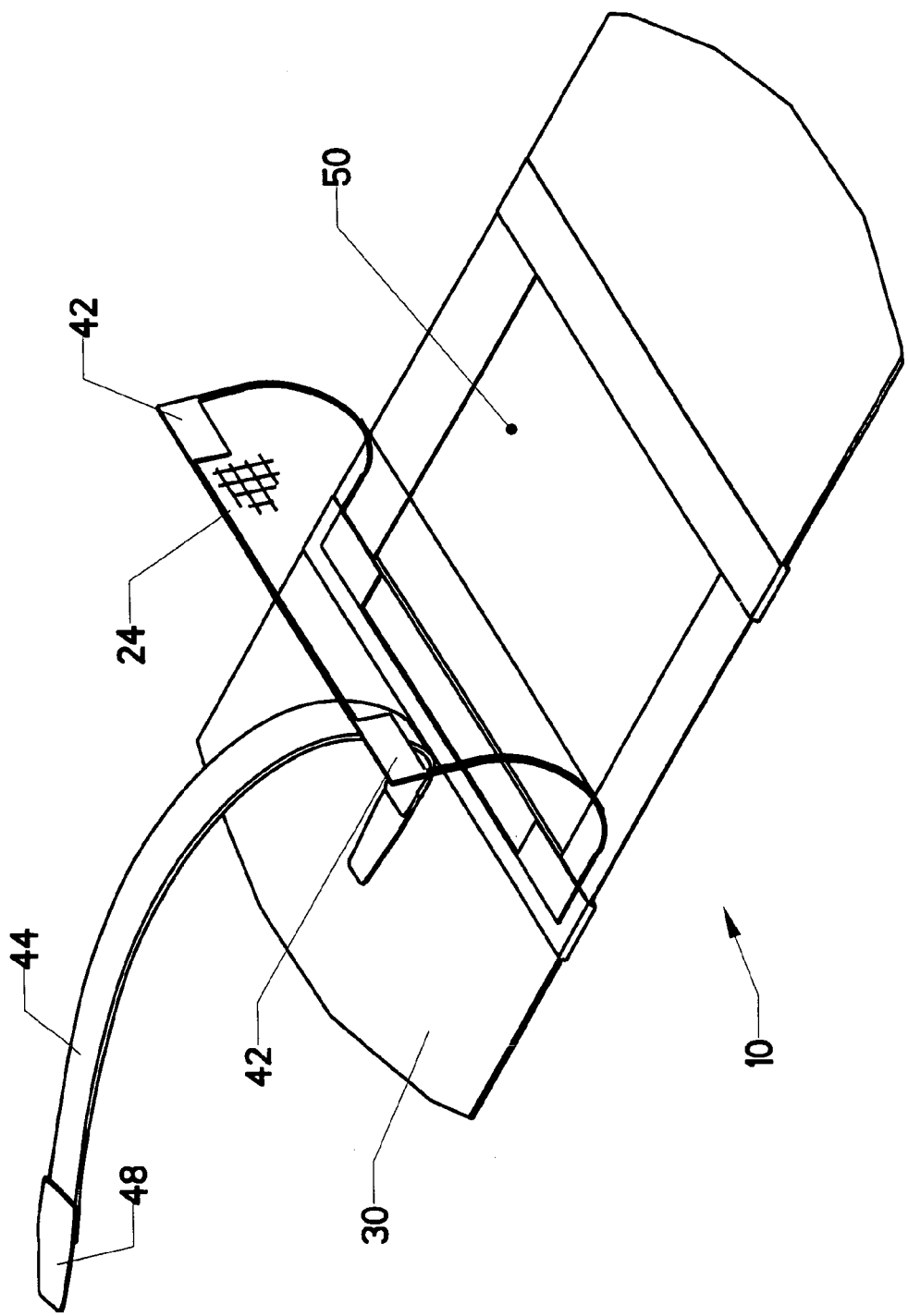
FIG. 4 is a perspective view, showing how the ventral window components can be removed to provide access.

FIG. 4 shows how the mesh panel and middle strap can be opened. While both these pieces can be removed in their entirety, it is often convenient to detach only one side and roll them back as shown. This provides good access to opening 50.

Figure 5:
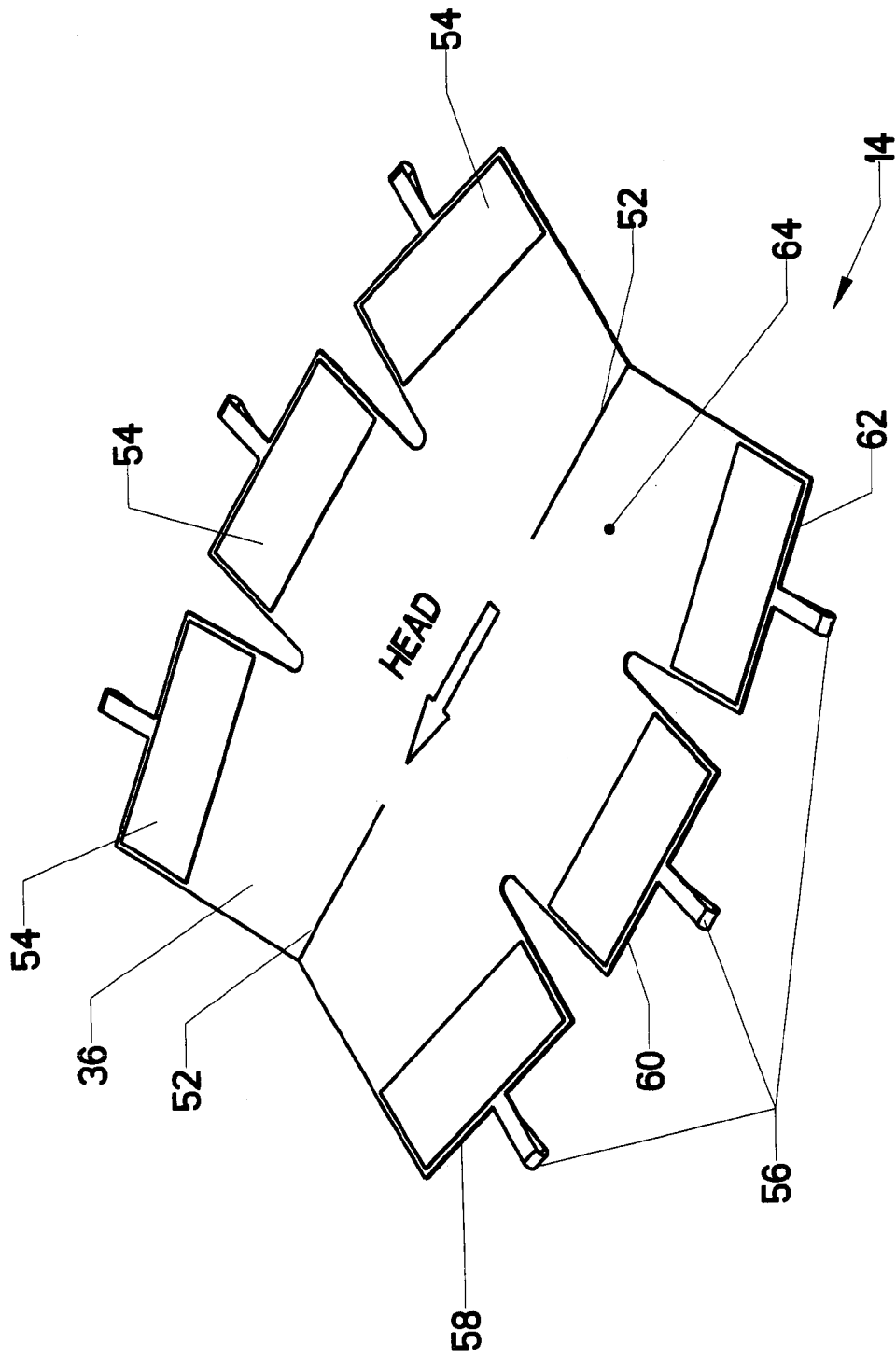
FIG. 5 is a perspective view, showing the components of the ventral window cover.

FIG. 5 shows inner surface 36 of ventral window cover 14. A dart seam 52 is provided at both the anterior and posterior extremes of central portion 64. This allows the panel to assume the contoured shape shown (where the two side edges curve). Those skilled in the art will realize that the dart seams allows the ventral window cover to more accurately follow the convex shape of a horse's chest and abdomen. The dart seams are created by laying out a flat pattern, then cutting out two vee-shaped darts, then sewing the sides of the darts together (or otherwise bonding them together). The result is a slightly concave surface (when viewed from the perspective of FIG. 5) that can curve in two planes.

The two dart seams are preferably asymmetric, since the horse's abdomen will be smaller than its chest. Thus, it is important to put the device in the correct orientation. Hence, it is helpful to provide the printed graphic ("HEAD") to help the user properly orient the device.

Each lateral side of the ventral window cover has three tabs—front tab 58, middle tab 60, and rear tab 62. The outer extreme of each tab includes a hook panel 54 and a lanyard 56. The hook panels are positioned to engage the VELCRO® loops on outer surface 30 of main wrap 10. The lanyards are used to pull the window cover taut before the VELCRO® features are engaged.

Figure 6:
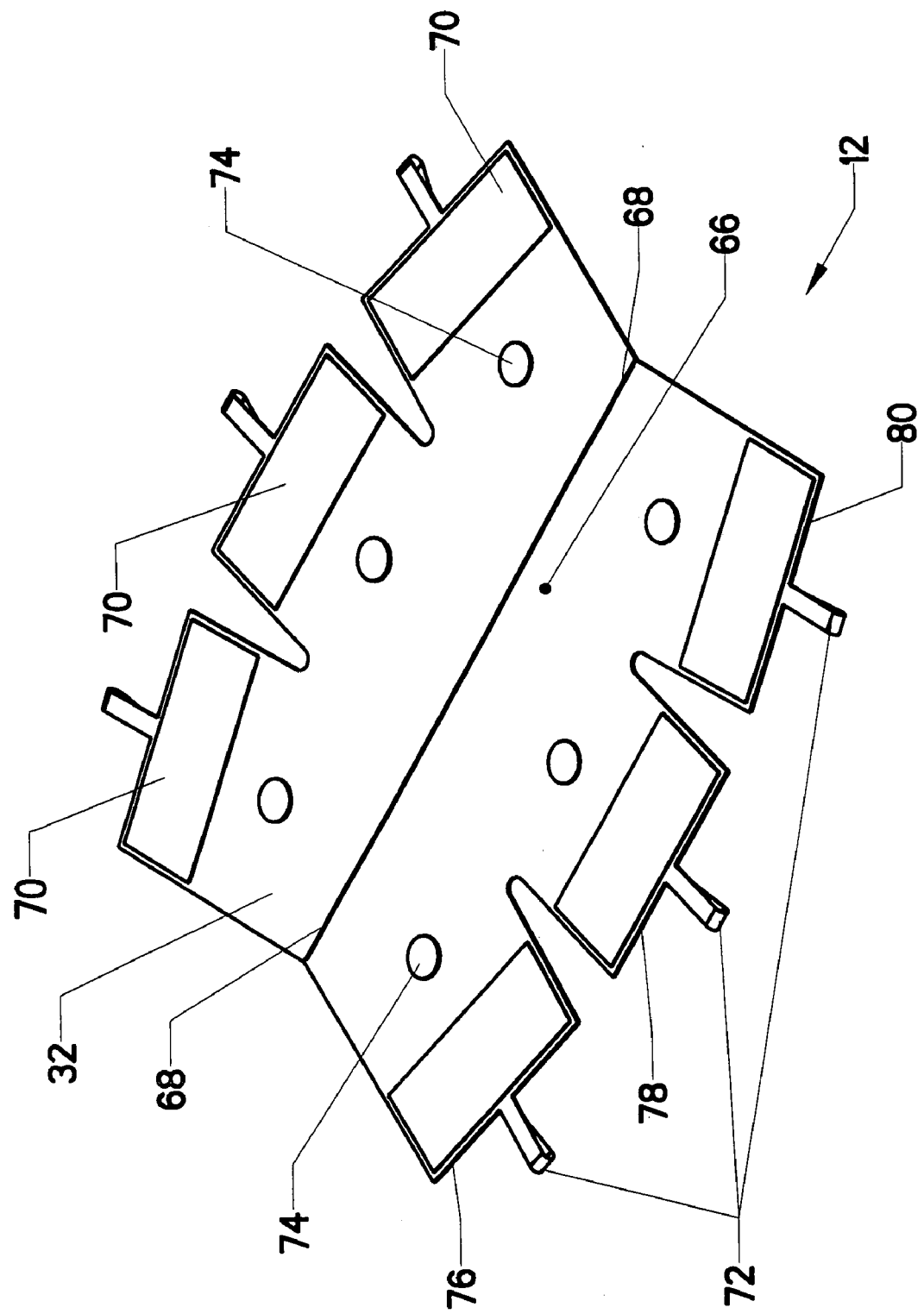
FIG. 6 is a perspective view, showing the components of the saddle bridge.

FIG. 6 shows inner surface 32 of saddle bridge 12. It also includes a pair of dart seams 68 at both the anterior and posterior extremes of central portion 66. These allow the panel to be curved in two planes, as for the ventral window cover. However, given the physiology of the concave shape of a horse's back, it is not so important to make the device asymmetric. Thus, the two darts may be the same. Each lateral side of the saddle bridge has three tabs—front tab 76, middle tab 78, and rear tab 80. The outer extreme of each tab includes a hook panel 70 and a lanyard 72. The hook panels are positioned to engage the VELCRO® loops on outer surface 30 of main wrap 10. The lanyards are used to pull the window cover taut before the VELCRO® features are engaged.

Figure 7:
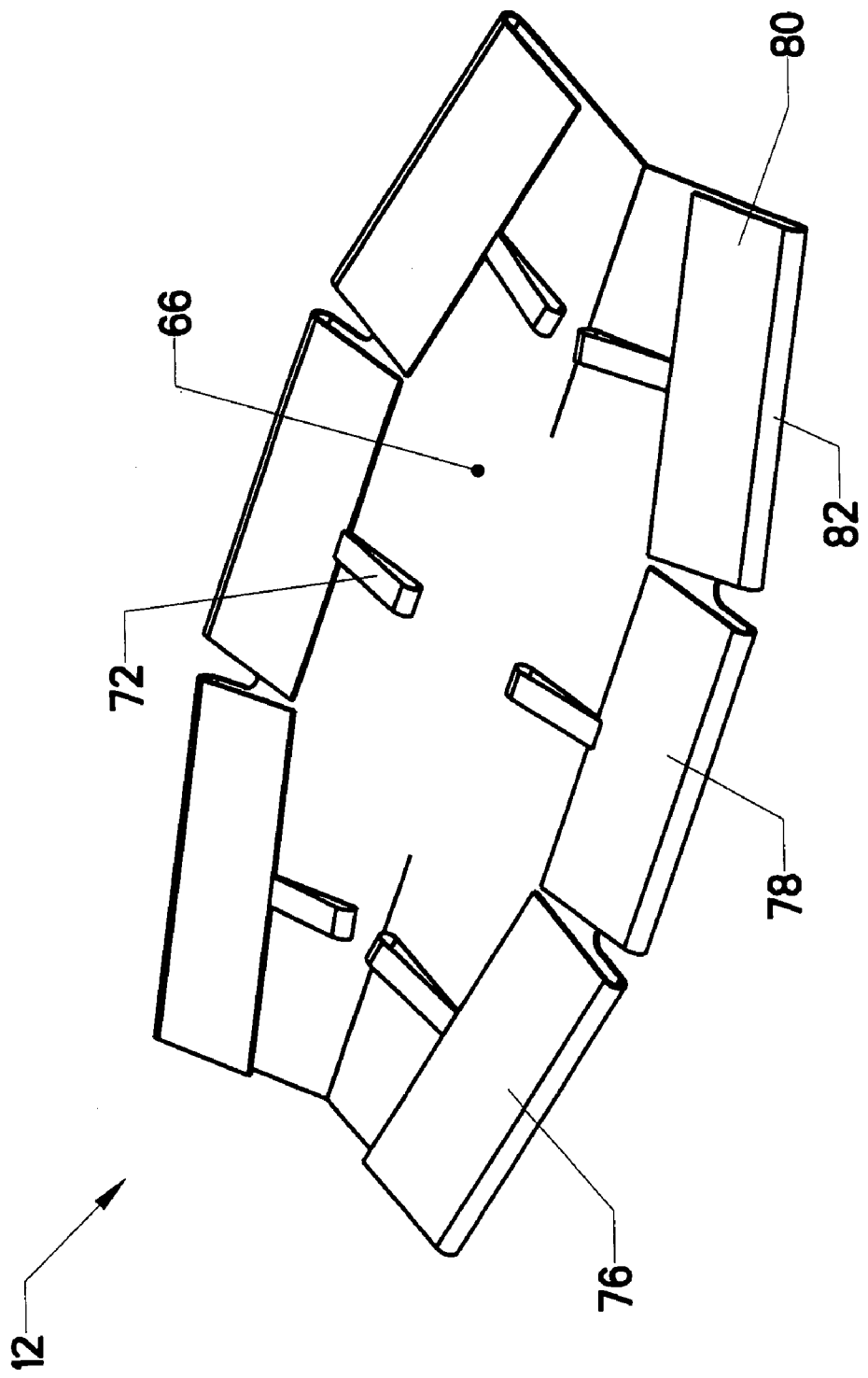
FIG. 7 is a perspective view, showing how the saddle bridge's six tabs can be folded over and secured in place.

A loop panel 74 is also located proximate each of the six tabs. These are small patches of VELCRO® loop material. They allow the six tabs to be folded in and temporarily attached in a folded state (with each hook panel 70 being attached to a loop panel 74). FIG. 7 shows the saddle bridge with the tabs in the folded and locked state. It will remain in this position until the tabs are pulled free. This folded state can be helpful in the installation process, which will be described shortly.

FIG. 8 shows more detail regarding brace 16. All its components have an inner surface 84 and an outer surface 86. Outer surface 86 is covered in fine VELCRO® loop material. Four hook panels 88 are provided to attach the brace. These hook panels are completely detachable from the brace. This feature allows the user to trim the length of the upper and lower wings. If a wing is too long, the user pulls its hook panel 88 loose, then cuts it to the desired length. The user then presses the hook panel back against outer surface 86. A portion of each hook panel should cover the end of a wing and a portion should be positioned to extend beyond the wing. The VELCRO® hooks on this extended portion will be used to engage the VELCRO® loops on the outer surface of the main wrap, the saddle bridge, and/or the ventral window cover.

Figure 8B:
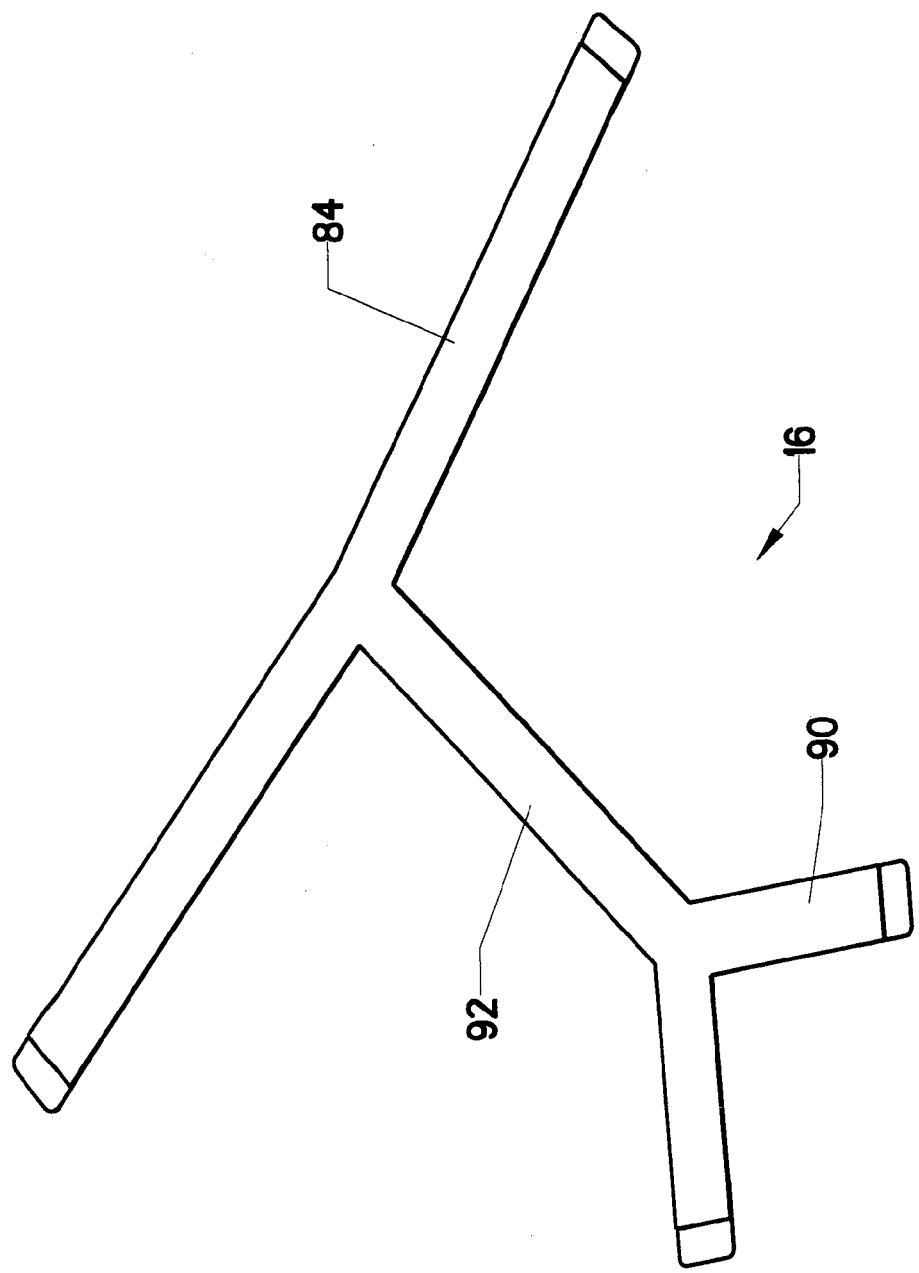
FIG. 8B is a perspective view, showing an alternate embodiment of the brace.

FIG. 8B shows the same brace with the angles defining the joints between the components being altered somewhat. Such alterations may need to be made to accommodate varying equine physiology. However, the brace shown in FIG. 8B functions int he same manner as the brace shown in FIG. 8.

Having described the components in detail, the application of the device to a horse will be explained. The device will typically be installed after some type of abdominal surgery on the horse. FIG. 9 shows two components ready for installation. Saddle bridge 12 has been placed in the configuration shown in FIG. 7 (though it is inverted from the orientation of FIG. 7). The two ends of main wrap 10 have been rolled into two rolls 96 flanking ventral window 22, so that the main wrap is now compact and easy to handle.

FIG. 10 shows the horse, which will typically be held by an attendant using a halter around the horse's head. Two more people then stand beside the horse on opposite sides of the horse's withers. The main wrap is passed under the horse's abdomen, with inner surface 28 facing the horse. The ventral access window is centered over the horse's abdomen. Each roll 96 is then unrolled up the horse's two sides. The rolling stays 18 help hold the rolls fairly rigid so that they are easy to manipulate.

FIG. 11 shows the main wrap after the two rolls 96 have been completely unrolled. The elastic panel comprising the main wrap has a gap in its dorsal region. The panel actually terminates in a first lateral dorsal edge 25 (visible to the viewer in FIG. 11 and also labeled in FIG. 1) and a second lateral dorsal edge 27 on the other side of the horse (also labeled in FIG. 1). The two lateral dorsal edges are proximate the pockets used to house the two rolling stays.

At this point, each of the two attendants flanking the horse pulls a bridging strap 26 over the horse's back and presses the VELCRO® hooks on the underside of each bridging strap against the VELCRO® loop material on outer surface 30. The gap in the dorsal region of the elastic panel is thereby temporarily secured. The bridging straps can be left in place while the users place the next component.

Figure 12:
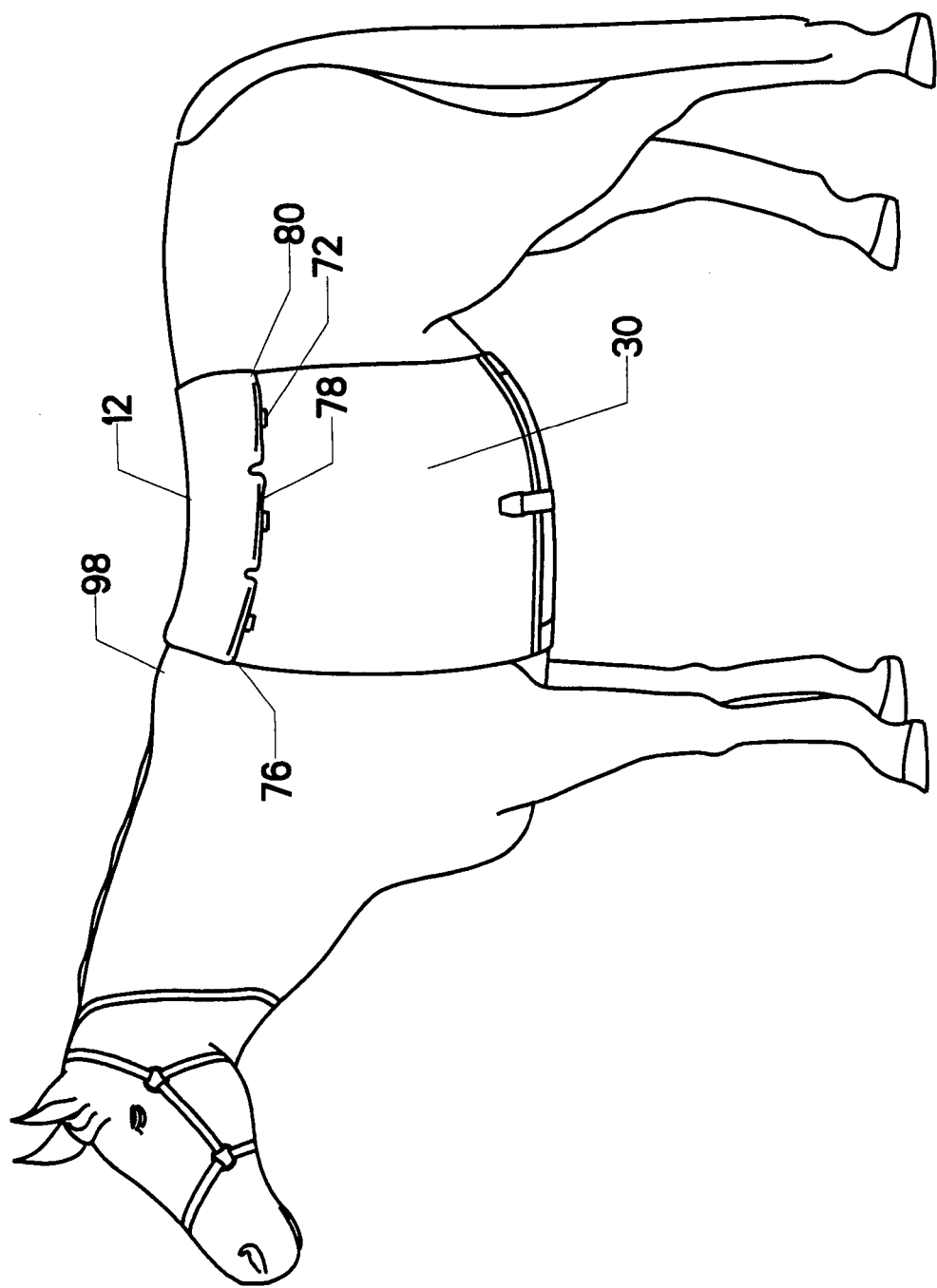
FIG. 12 is a perspective view, showing the placement of the saddle bridge over the top of the main wrap.

FIG. 12 shows saddle bridge 12 placed over the horse's back and spanning the gap in the main wrap. Because the six tabs on the saddle bridge are folded under and secured, it does not "stick" to anything. The user may therefore manipulate the saddle bridge and obtain the desired position.

The saddle bridge is preferably used to tighten the main wrap in a controlled fashion. The tightening sequence will be dictated by the particular horse's anatomy, and the user's preferred approach (The users will often be directed by a veterinarian). Thus, the following should be viewed as exemplary, rather than indicating the only method of application.

The user will often want to secure the two middle tabs 78, since these will tighten the main wrap around the horse's largest circumference. One person on each side pulls the lanyard on the two middle tabs 78 to unfold the middle tabs and pull them outward. The two people then pull the lanyards out and down (making sure that the hook panels 70 remain clear of the VELCRO® loop material on the main wraps outer surface) until the desired tension is reached (The tabs will stretch considerably). They then press the two middle tabs against the main wrap, whereupon the VELCRO® interface will secure the two middle tabs. This action effectively tightens the middle of the main wrap around the largest circumference of the horse.

Figure 13:
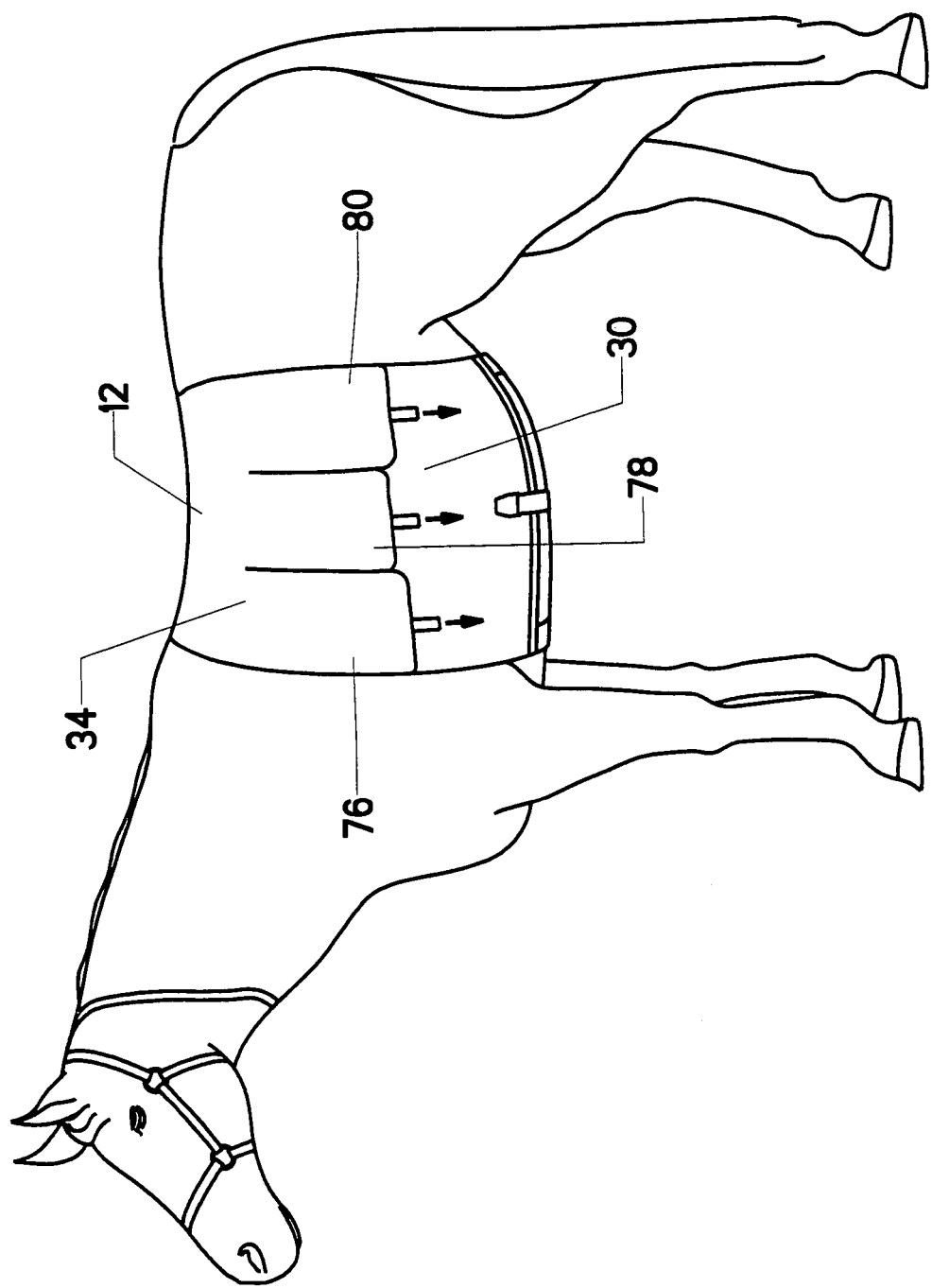
FIG. 13 is a perspective view, showing the use of the saddle bridge's tabs to place tension on the main wrap.

Next, the two people detach the two front tabs 76 and stretch and attach these tabs to secure the main wrap around the portion of the horse that is customarily occupied by a saddle girth. Finally, the two people detach, adjust, and secure the two rear tabs 80 to secure the main wrap around the horse's abdomen. FIG. 13 shows the saddle bridge with all three sets of tabs attached to the main wrap.

While it may be possible to create the desired profile of tension in the main wrap on initial installation, it may often be necessary to adjust the tabs through several iterations. This may easily be done by using a lanyard to pull a particular tab loose. The tension provided by that tab is then modified and the tab is reattached. The independent nature of the six tabs, in combination with the elastic nature of the material used, allows the assembly to accommodate many variations is equine anatomy. The reader will observe in FIG. 13 that the three tabs facing the viewer have been independently adjusted to different lengths.

Figure 14:
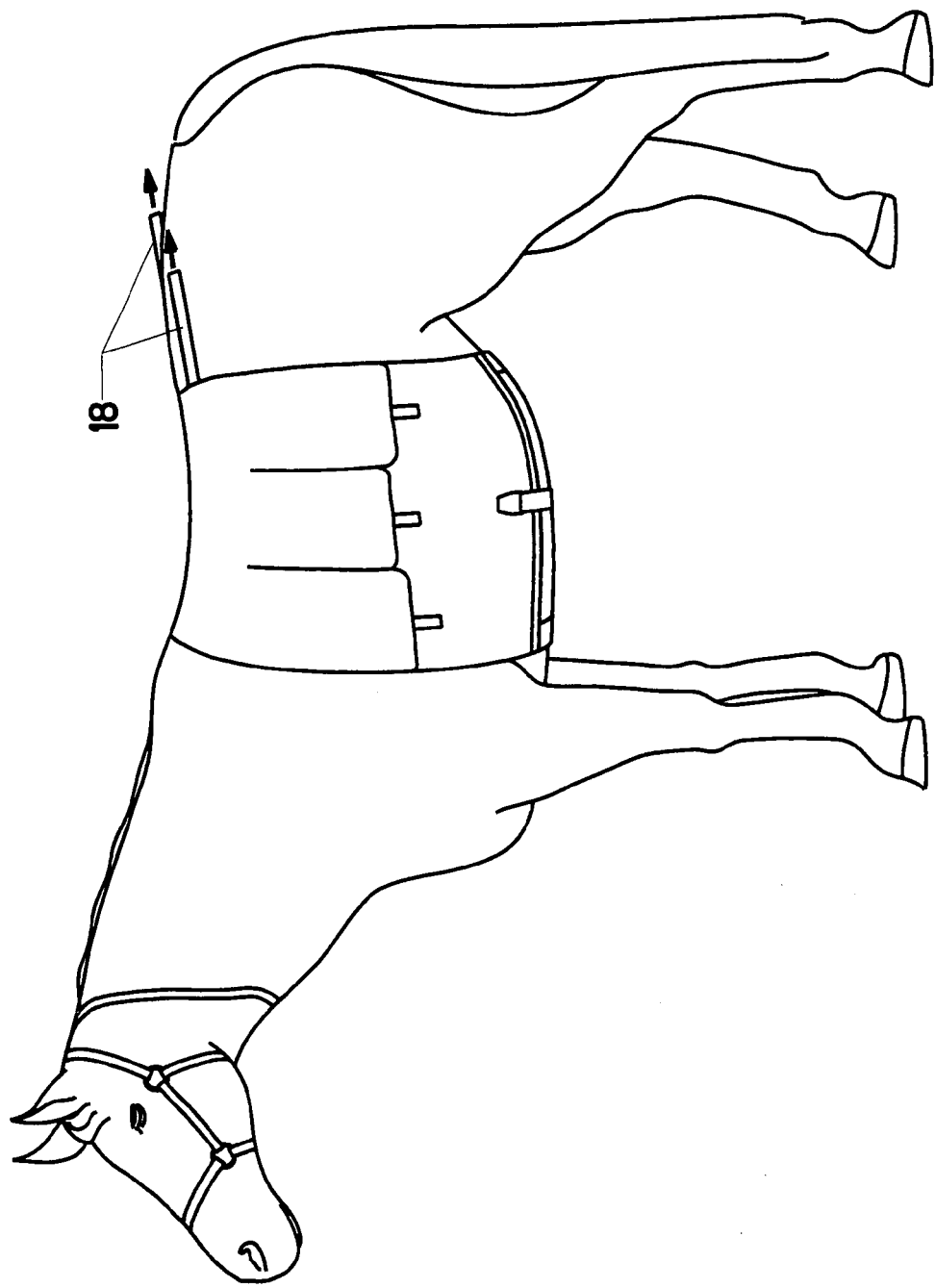
FIG 14 is a perspective view, showing the removal of the two rolling stays.

At some point in the installation process (generally after the saddle bridge has been installed), it may be desirable to remove the two rolling stays 18. The reader will recall from FIG. 2B that the two rolling stays may be pulled out of the two rolling stay pockets. FIG. 14 shows this operation. The rolling stay pockets are located high enough that the rolling stays are free to slide out over the horse's rump. They should then be stored for future use.

Figure 15:
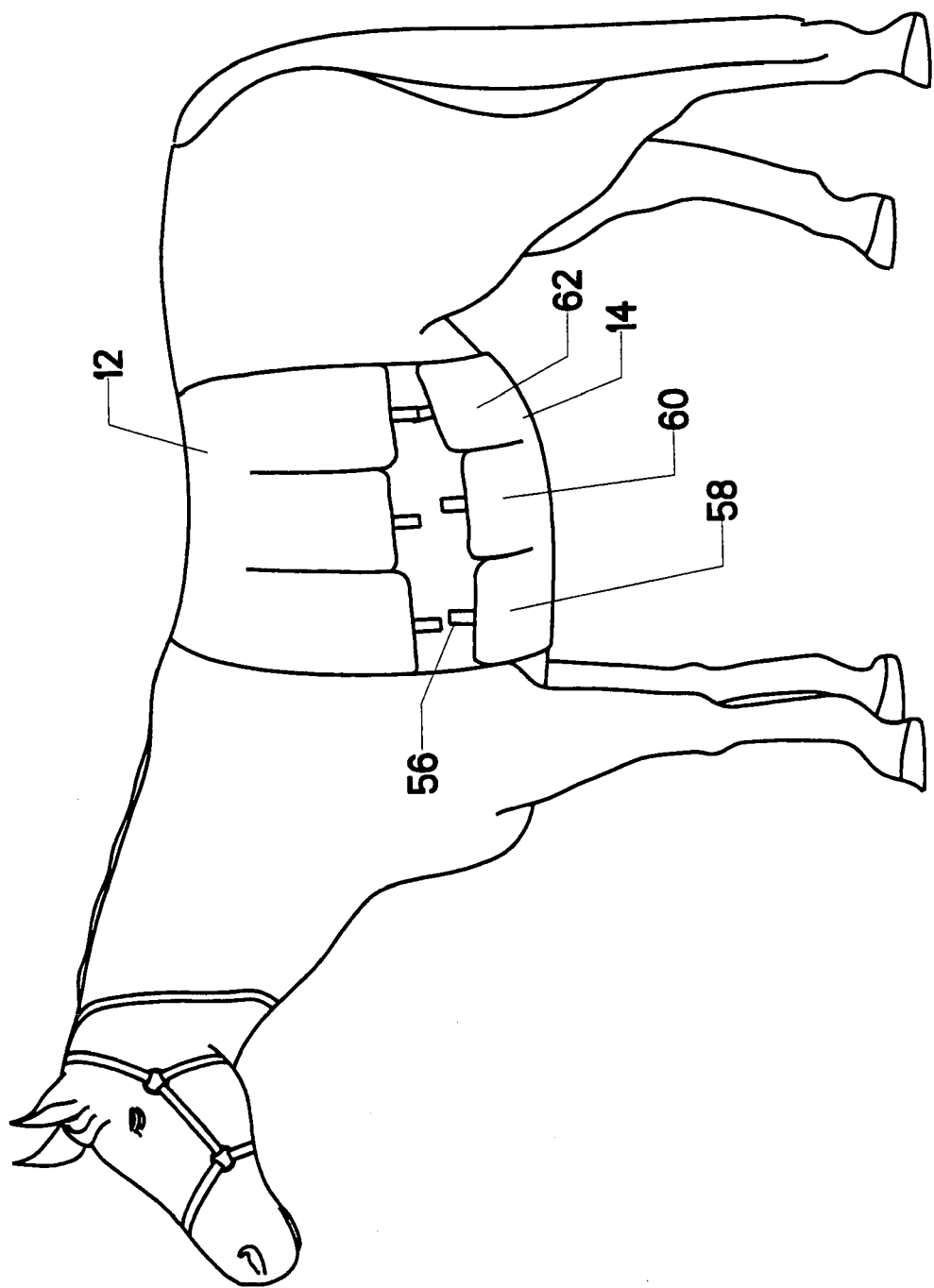
FIG. 15 is a perspective view, showing the placement of the ventral window cover.

FIG. 15 shows the installation of the ventral window cover. It is passed under the horse's abdomen and the three sets of tabs are then sequentially pulled taut and attached by pressing hook panels 54 (see FIG. 5) against the VELCRO® loop material on the outer surface of the main wrap. Like the saddle bridge, it may have to be iteratively tightened until the desired fit is achieved.

Figure 16:
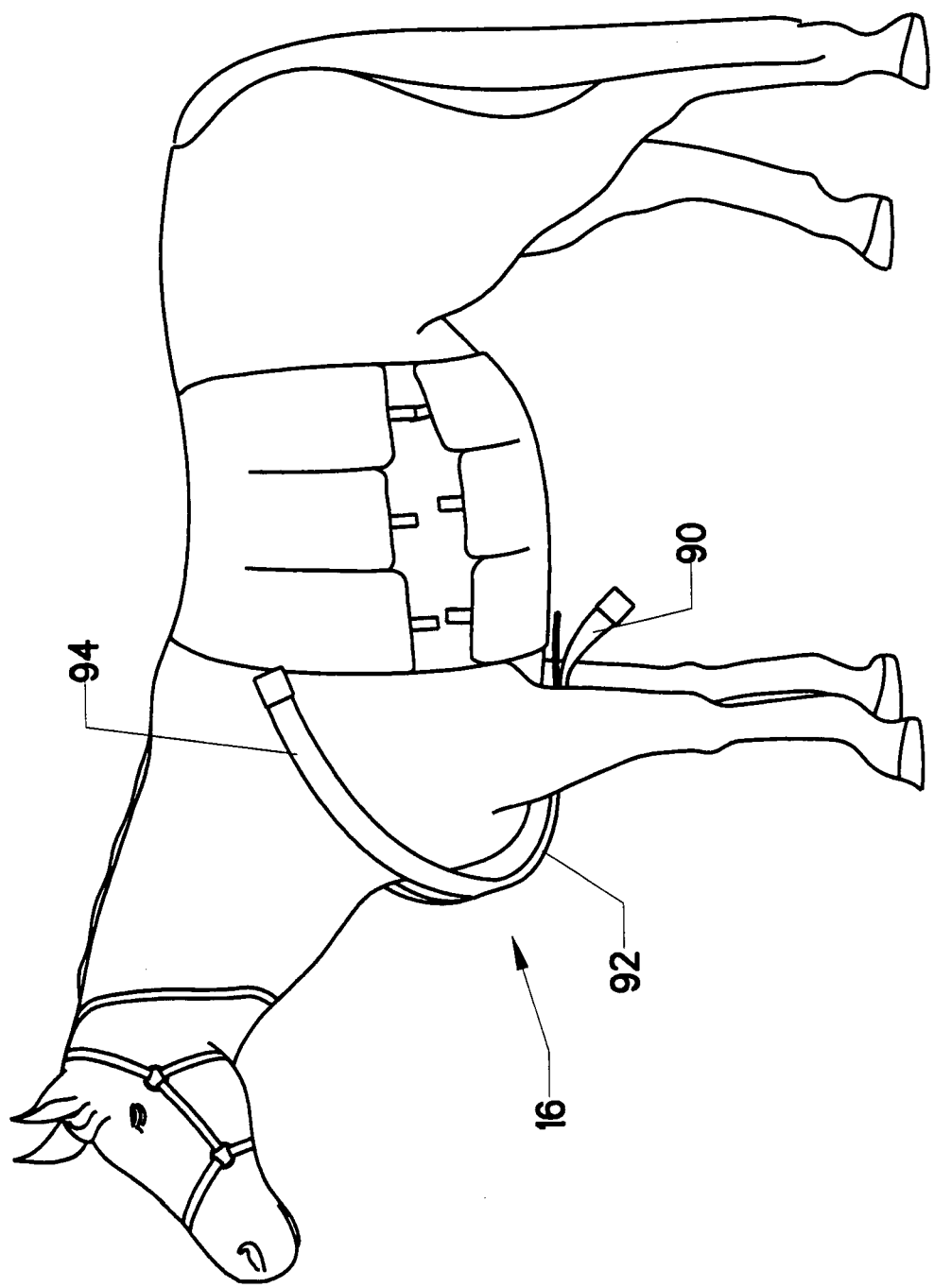
FIG. 16 is a perspective view, showing the placement of the brace.

Finally, brace 16 should be installed. FIG. 16 shows this step. Sternal bridge 92 is passed between the horse's front legs. The two lower wings 90 are then positioned over the lower chest, while the two upper wings 94 are posited over and beyond the shoulders. The wings are drawn taut and the four hook panels 88 are then pressed against the outer surface of the main wrap, saddle bridge, and or ventral window cover (depending on the position desired).

FIG. 17 shows the brace installed. The two upper wings 94 should pass over the point of the shoulder 100, while the sternal bridge should lie below carotid notch 102. In this location, the brace will be stabilized by the horse's own anatomy. It prevents the main wrap from migrating rearward. With the installation complete, the horse is free to move about without fear of dislodging the wrap. Thus, the horse need not be confined during the recuperation process.

Figure 18:
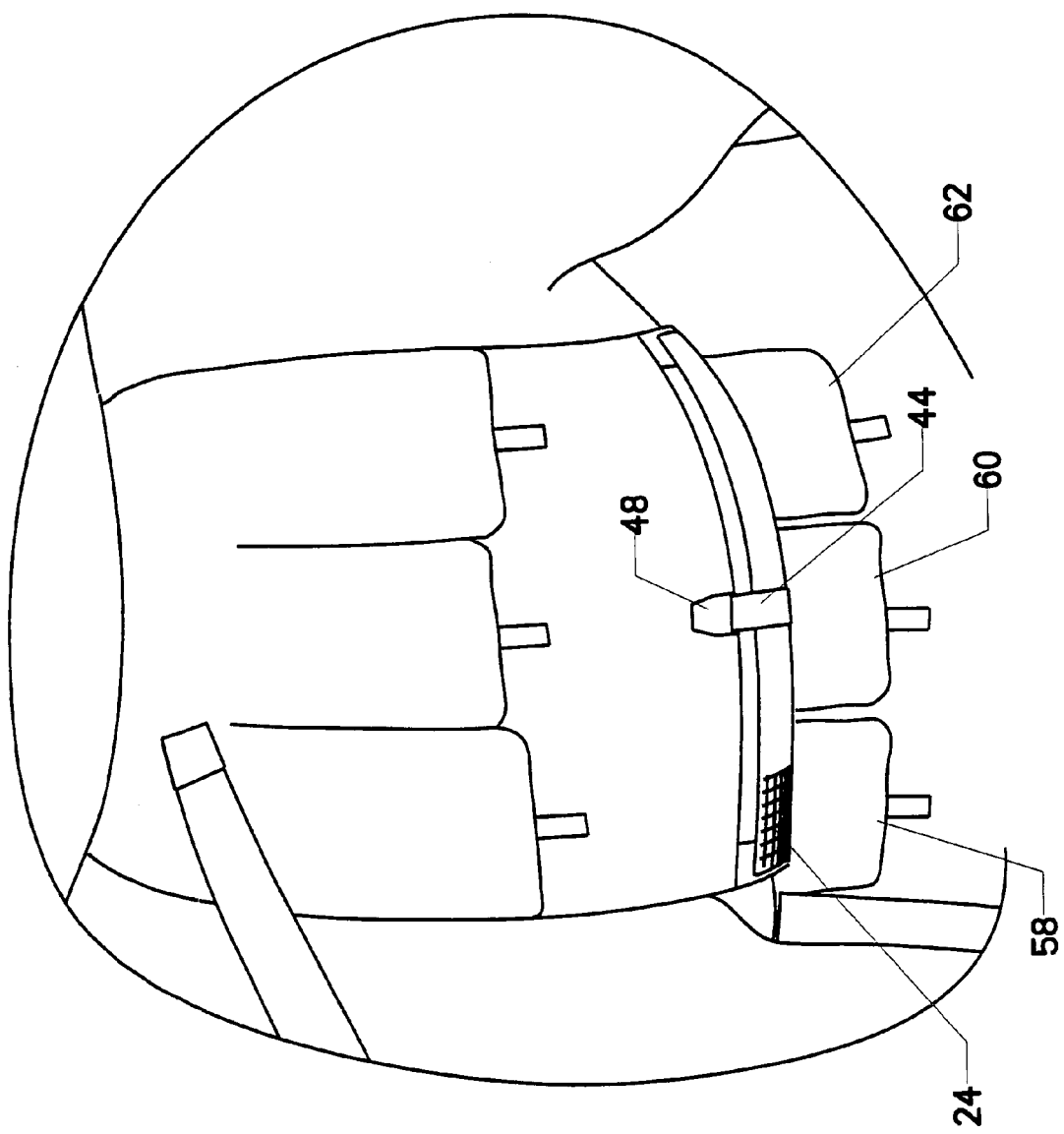
FIG. 18 is a perspective view, showing the opening of the ventral window cover with the bandaging system in place.
Figure 19:
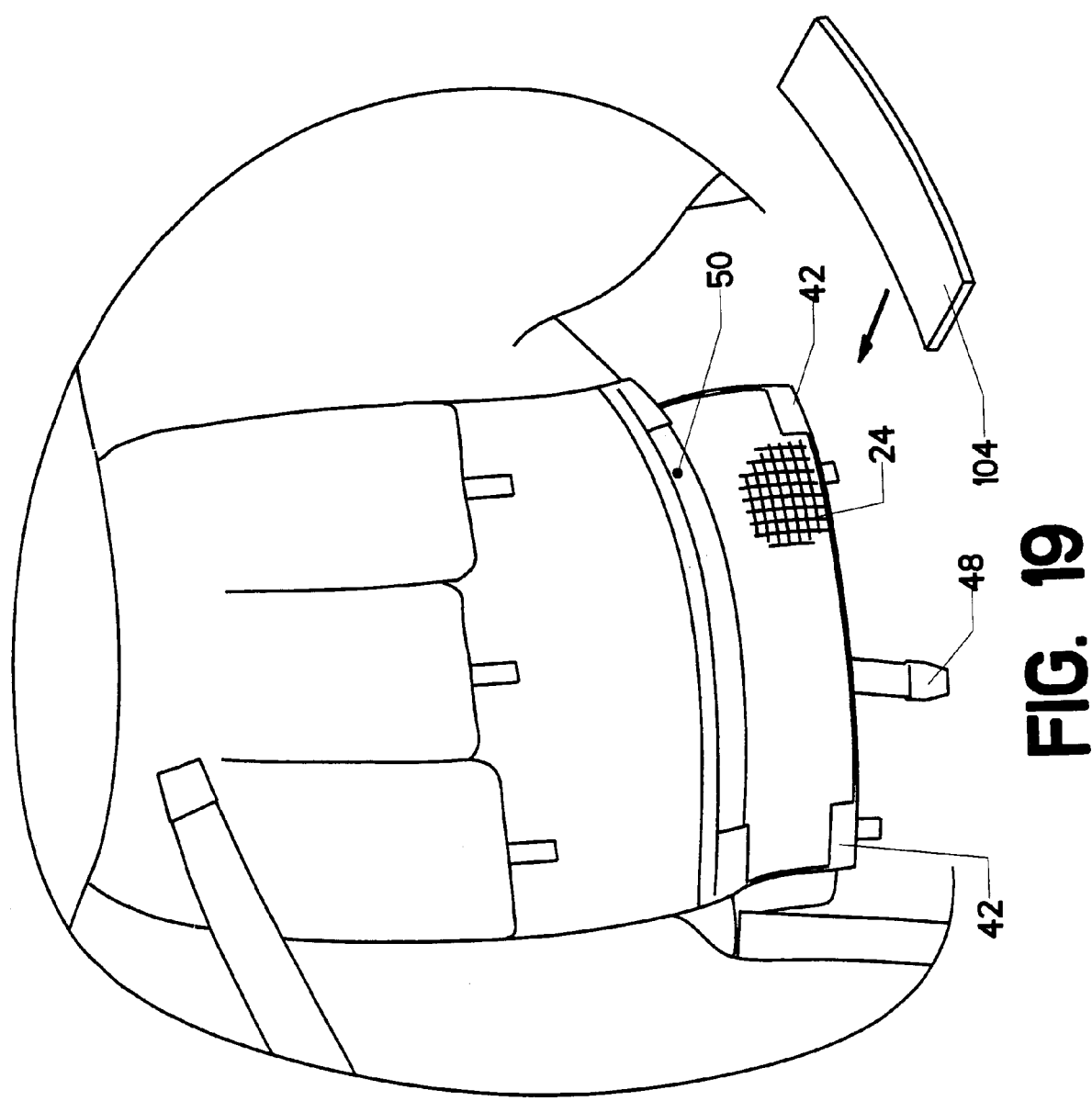
FIG. 19 is a perspective view, showing the opening of the mesh panel to provide access to the horse's abdomen.

One of the invention's main features is the inclusion of the ventral access window. This allows access to the horse's ventral region while the bandage remains in place. FIGS. 18 and 19 show the access process. In FIG. 18, the three nearside tabs on the ventral window cover have been detached, allowing the window cover to drop open. The user next grasps hook tab 48 and pulls the near end of middle strap 44 loose. Finally, the user grasps the near side of mesh panel 24 and pulls it free.

FIG. 19 shows the resulting configuration, with one side of the mesh panel and the middle strap dropped open. Opening 50 then provides unfettered access to the horse's abdomen. An old dressing can then be removed. Sutures or staples can be inspected and cleaned. A new dressing 104 can then be slipped into position. The mesh panel, middle strap, and ventral window cover are then replaced in sequence. The ventral window cover can be retightened as desired.

During this process, abdominal support is still provided by the balance of the main wrap. There is only a brief period where the wound site itself is unsupported. This period ends when the ventral window is closed.

Those skilled in the art will realize that the ventral window cover need not be completely removable from the rest of the main wrap. It could be stitched down one side, leaving the other side removable. However, providing a completely removable ventral window cover is the preferred embodiment.

Although the preceding description contains significant detail, it should not be viewed as limiting the invention but instead as providing illustrations of the preferred embodiments of the invention. As an example, buckles and clasps could be substituted for the use of the VELCRO® interfaces without altering the basis structure of the invention. These would certainly be less convenient, but they could be used in the same fashion. Thus, the scope of the present invention should thus be defined by the following claims rather than any specific examples given.

The invention claimed is:

1. A compressive wrap configured to be applied to a horse, said horse including a concave dorsal region, a convex ventral region, a pair of front legs, a sternal region between said pair of front legs, a pair of back legs, and two shoulder points, comprising:
   a. a main wrap having an outer surface, with said outer surface being at least partially covered in loop material;
   b. said main wrap including a first lateral dorsal edge and a second lateral dorsal edge, and being configured to pass around said horse's ventral region between said pair of front legs and said back legs and extend upwards along the sides of said horse so that said first lateral dorsal edge lies along a first side of said horse and said second lateral dorsal edge lies along a second side of said horse;
   c. said main wrap including a ventral window
   d. a ventral window cover configured to selectively cover said ventral window, said ventral window cover having a first side and a second side, and said ventral window cover having an inner surface;
   e. said first side of said ventral window cover including a first plurality of independently adjustable tabs, with each of said adjustable tabs having a panel of hook material on said inner surface positioned to mate to said loop material on said outer surface of said main wrap;

f. said second side of said ventral window cover including a second plurality of independently adjustable tabs, with each of said adjustable tabs having a panel of hook material on said inner surface positioned to mate to said loop material on said outer surface of said main wrap;

g. a saddle bridge, having a first side, a second side, and an inner surface, wherein said first side of said saddle bridge is selectively connected to said main wrap proximate said first lateral dorsal edge and said second side of said saddle bridge is selectively connected to said main wrap proximate said second lateral dorsal edge;

h. said first side of said saddle bridge including a third plurality of independently adjustable tabs, with each of said adjustable tabs having a panel of hook material on said inner surface positioned to mate to said loop material on said outer surface of said main wrap; and i. said second side of said saddle bridge including a fourth plurality of independently adjustable tabs, with each of said adjustable tabs having a panel of hook material on said inner surface positioned to mate to said loop material on said outer surface of said main wrap.

2. A compressive wrap as recited in claim 1, further comprising:
at least one bridging strap linking said first lateral dorsal edge to said second lateral dorsal edge.

3. A compressive wrap as recited in claim 2, wherein said at least one bridging strap is selectively removable.

4. A compressive wrap as recited in claim 3, further comprising:
a. a first rolling stay attached to said first lateral dorsal edge;
b. a second rolling stay attached to said second lateral dorsal edge; and
c. wherein said first and second rolling stays are substantially more rigid than said main wrap.

5. A compressive wrap as recited in claim 4, wherein said first and second rolling stays are removable.

6. A compressive wrap as recited in claim 1, wherein each of said plurality of tabs includes a lanyard.

7. A compressive wrap as recited in claim 1, wherein said inner surface of said saddle bridge further comprises a plurality of loop panels, with each of said plurality of loop panels being located proximate one of said independently adjustable tabs, so that each of said independently adjustable tabs can be folded over and locked to one of said loop panels by pressing said panel of hook material on each of said independently adjustable tabs against said loop panel.

8. A compressive wrap as recited in claim 1, wherein said saddle bridge is shaped to conform to said concave shape of said horse's dorsal region.

9. A compressive wrap as recited in claim 1, wherein said ventral window is bounded by a first lateral ventral edge and a second lateral ventral edge and wherein each of said first and second lateral ventral edges is reinforced by a window stay.

10. A compressive wrap as recited in claim 1, further comprising a removable middle strap passing over said ventral window but lying beneath said ventral window cover.

11. A compressive wrap as recited in claim 1, further comprising a mesh panel removably attached over said ventral window and beneath said ventral window cover.

12. A compressive wrap as recited in claim 11, further comprising a removable middle strap attached over said mesh panel and beneath said ventral window cover.

13. A compressive wrap as recited in claim 1, wherein:
said ventral window cover is made of elastic material.

14. A compressive wrap as recited in claim 1, further comprising a brace configured to pass around said horse's pair of front legs and over said horse's shoulder points, and thereafter be attached to said elastic panel, said saddle bridge, said ventral window cover, or any combination thereof, thereby preventing said compressive wrap from moving rearward on said horse.

* * * * *